United States Patent
Ferritto et al.

(10) Patent No.: US 6,774,179 B2
(45) Date of Patent: *Aug. 10, 2004

(54) ENCAPSULATION OF ACTIVES IN CORE-SHELL AND GEL PARTICLES

(75) Inventors: Michael Salvatore Ferritto, Midland, MI (US); Zuchen Lin, Midland, MI (US); Janet Mary Smith, Bay City, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/017,976

(22) Filed: Dec. 13, 2001

(65) Prior Publication Data

US 2003/0050393 A1 Mar. 13, 2003

Related U.S. Application Data

(60) Provisional application No. 60/256,533, filed on Dec. 18, 2000.

(51) Int. Cl.$^7$ ............................. C08L 83/04; A61K 7/00
(52) U.S. Cl. ..................... 524/860; 524/837; 524/838; 524/863; 524/864; 525/474; 525/476; 424/401
(58) Field of Search ................................. 524/837, 838, 524/860, 863, 864; 525/474, 476; 424/401

(56) References Cited

U.S. PATENT DOCUMENTS

| | | | |
|---|---|---|---|
| 4,987,169 A | | 1/1991 | Kuwata et al. ............. 524/267 |
| 5,017,297 A | * | 5/1991 | Spyropoulos et al. ........ 428/391 |
| 5,665,804 A | * | 9/1997 | Hill et al. .................... 524/268 |
| 5,760,116 A | | 6/1998 | Kilgour et al. ............. 524/268 |
| 5,811,487 A | | 9/1998 | Schulz, Jr. et al. ......... 524/862 |
| 5,889,108 A | | 3/1999 | Zhang ........................ 524/862 |
| 5,948,855 A | | 9/1999 | Lin et al. .................... 524/837 |
| 6,238,657 B1 | | 5/2001 | Lin et al. .................. 424/70.12 |
| 6,248,855 B1 | * | 6/2001 | Dalle et al. .................... 528/26 |
| 6,653,378 B2 | * | 11/2003 | Ferritto et al. .............. 524/267 |

FOREIGN PATENT DOCUMENTS

| | | | | |
|---|---|---|---|---|
| EP | 0393634 A2 | | 10/1990 | ............. C08J/3/12 |
| EP | 0739928 A2 | | 10/1996 | ............. C08J/3/03 |
| EP | 0893467 A2 | | 1/1999 | ............. C08J/3/03 |
| EP | 1020494 A1 | | 7/2000 | ........... C08L/83/12 |
| EP | 1048686 A2 | | 11/2000 | .......... C08G/77/46 |
| GB | 1296136 A | * | 11/1972 | |
| WO | WO 95/35183 | | 12/1995 | .......... B23K/20/12 |
| WO | WO 99/26585 | | 6/1999 | ............ A61K/7/00 |

* cited by examiner

Primary Examiner—Jeffrey B. Robertson
(74) Attorney, Agent, or Firm—Alan Zombeck

(57) ABSTRACT

This invention pertains to silicone core-shell or gel particles that contain active ingredients. The silicone particles are produced by emulsifying and reacting a composition comprising a siloxane have a first reactive group, a crosslinker having a second reactive group, at least one emulsion liquid, a surfactant and an active ingredient. The active ingredient is encapsulated in the silicone particle and are useful in personal care products, textiles, auto care products, and laundry products for the delivery of active ingredients.

20 Claims, No Drawings

ENCAPSULATION OF ACTIVES IN CORE-SHELL AND GEL PARTICLES

This application claims the benefit of U.S. Provisional Application No. 60/256,533 filed Dec. 18, 2000.

FIELD OF THE INVENTION

This invention relates to the formation of silicone core-shell or gel particles that can be used encapsulate actives.

BACKGROUND OF THE INVENTION

In personal care formulations it has become desirable to use low viscosity silicones to impart a number of benefits to the formulation. However, because of the addition of the low viscosity silicone, there must be additionally added a thickener to the personal care formulation. Certain silicone polymers have found utility as the thickening agent because they can be used in the quantities necessary to thicken the composition without degrading the properties of the personal care formulation. Typically, the silicone polymer and low viscosity silicone are combined to form a paste. This paste can then be used in the personal care formulation. Such silicone polymers are described in U.S. Pat. No. 4,987,169 to Kuwata et al., U.S. Pat. No. 5,760,116 to Kilgour et al., U.S. Pat. No. 5,811,487 to Schulz, Jr. et al. and U.S. Pat. No. 5,889,108 to Zhang and U.S. Pat. No. 6,238,657 to Lin et al.

This invention relates to the formation of silicone core-shell or gel particles that can be used to encapsulate actives. The resulting encapsulated actives can be used in personal care formulations.

SUMMARY OF THE INVENTION

This invention relates to the formation of silicone core-shell or gel particles that can be used encapsulate actives. The silicone particles are produced by emulsifying and reacting a composition comprising (I) a siloxane oligomer or polymer having units of

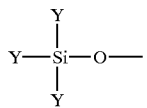

where Y independently is
O (oxygen radicals);
R' is selected from the group consisting of an alkyl group with 1 to 30 C atoms, an aryl group having 6 to 15 carbon atoms, an alkaryl group having 6 to 15 carbon atoms, and an aralkyl group having 6 to 15 carbon atoms;
Z is selected from epoxy-functional groups, chlorohydrin functional groups, or mixtures thereof;
Z' is a functional group that react with epoxy-functional groups or chlorohydrin functional groups (i.e. amine, hydroxyl); and
F is a functional group other than Z or Z',
with the proviso that at least 50 mol % of the Y groups in the siloxane are R', preferably methyl and there are at least two Z and/or Z' groups in the siloxane;
(II) a crosslinker wherein said crosslinker contains Z and/or Z' groups with the proviso that when Y in siloxane (I) contains Z groups, the crosslinker contains Z' groups; when Y in siloxane (I) contains Z' groups, the crosslinker contains Z groups; and when Y in siloxane (I) contains Z and Z' groups, the crosslinker contains Z groups, Z' groups or both;
(III) at least one emulsion liquid;
(IV) a surfactant; and
(V) and active ingredient.

The core-shell and gel particles produced by this method are useful in the encapsulation of actives. The encapsulated actives are useful in personal care products, textiles, auto care products, and laundry products for the delivery of active ingredients.

DETAILED DESCRIPTION OF THE INVENTION

This invention pertains to silicone core-shell or gel particles. The silicone particles are produced by emulsifying and reacting a composition comprising (I) a siloxane oligomer or polymer having units of

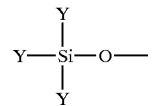

where Y independently is
O (oxygen radicals);
R' is selected from the group consisting of an alkyl group with 1 to 30 C atoms, an aryl group having 6 to 15 carbon atoms, an alkaryl group having 6 to 15 carbon atoms, and an aralkyl group having 6 to 15 carbon atoms;
Z is selected from epoxy-functional groups, chlorohydrin functional groups, or mixtures thereof;
Z' is a functional group that react with epoxy-functional groups or chlorohydrin functional groups (i.e. amine, hydroxyl); and
F is a functional group other than Z or Z',
with the proviso that at least 50 mol % of the Y groups in the siloxane are R', preferably methyl and there are at least two Z and/or Z' groups in the siloxane;
(II) a crosslinker wherein said crosslinker contains Z and/or Z' groups with the proviso that when Y in siloxane (I) contains Z groups, the crosslinker contains Z' groups; when Y in siloxane (I) contains Z' groups, the crosslinker contains Z groups; and when Y in siloxane (I) contains Z and Z' groups, the crosslinker contains Z groups, Z' groups or both;
(III) at least one emulsion liquid;
(IV) a surfactant; and
(V) an active ingredient.

Component (I) is a siloxane oligomer or polymer having units of

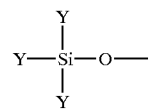

where Y independently is
O (oxygen radicals);
R' is selected from the group consisting of an alkyl group with 1 to 30 C atoms, an aryl group having 6 to 15 carbon atoms, an alkaryl group having 6 to 15 carbon atoms, and an aralkyl group having 6 to 15 carbon atoms;
Z is selected from epoxy-functional groups, chlorohydrin functional groups, or mixtures thereof;
Z' is a functional group that react with epoxy-functional groups or chlorohydrin functional groups (i.e. amine, hydroxyl); and F is a functional group other than Z or Z',
with the with the proviso that at least 50 mol % of the Y groups in the siloxane are R', preferably methyl and there are at least two Z and/or Z' groups in the siloxane.

Siloxane (I) can be comprised of $Y_3SiO$— units, $Y_2SiO_{2/2}$— units, $YSiO_{3/2}$— units and $SiO_{4/2}$ units wherein Y is as defined above. Preferable siloxane (I) primarily comprises $Y_2SiO_{2/2}$— units.

R' groups may be exemplified by, but not limited to, methyl, ethyl, propyl, isopropyl, butyl, isobutyl, and phenyl, preferably methyl.

Z groups may be exemplified by, but not limited to epoxy groups and chlorohydrin groups and mixtures thereof.

Z' groups may be exemplified by, but not limited to, amine groups and hydroxyl groups.

F groups may be exemplified by, but not limited to, polyether groups, quaternary ammonium salt groups, monohydroxy alcohol groups, polyhydroxy alcohol groups, carbohydrate groups, acrylate groups, ester groups, amide groups, carbonate groups, carboxylate groups, sulfonate groups, sulfate groups, halogen groups, trialkoxysilyl groups, the following functional groups wherein R is the same as R' defined above:

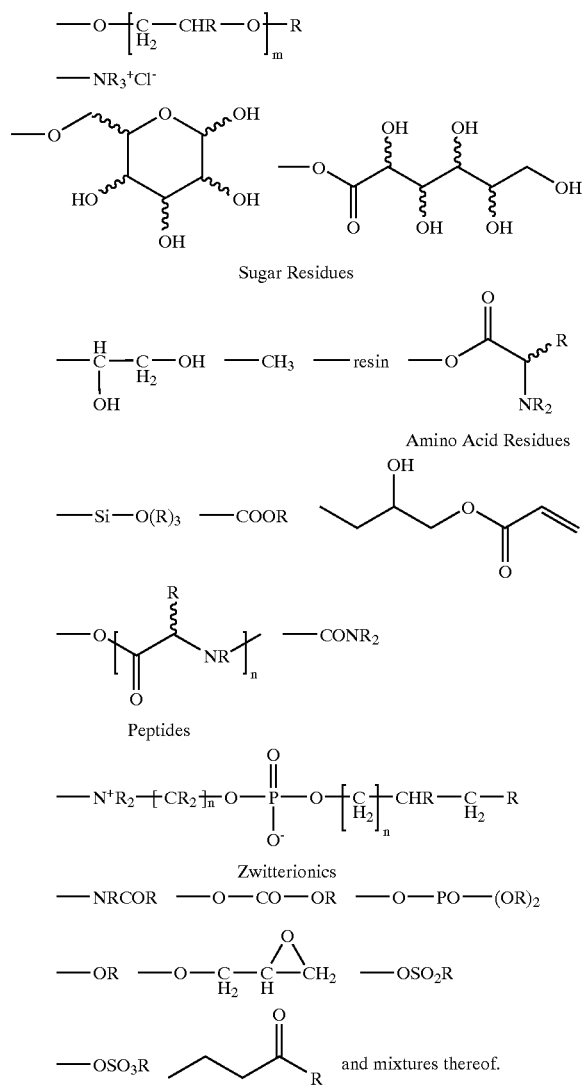

and mixtures thereof.

In Siloxane (I), there must be at least two reactive groups selected from Z and/or Z'. Preferably the reactive group is Z' and even more preferable the reactive group is an amine functional group.

Amine functional silicones that may be useful typically are of the formula

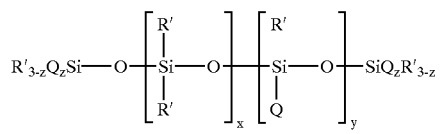

wherein R' is independently an alkyl group with 1 to 30 C atoms, an aryl group having 6 to 15 carbon atoms, an alkaryl group having 6 to 15 carbon atoms, and an aralkyl group having 6 to 15 carbon atoms with the proviso that at least 50% of the total number of R' groups are methyl; Q is an amine functional substituent of the formula —R"A wherein R" is a divalent alkylene radical having 3 to 6 carbons and A is a monovalent radical selected from the group consisting of —NR''', and —NR'''$(CH_2)_b$NR$_2$'''; wherein R''' denotes hydrogen or an alkyl group having 1 to 4 carbons, and b is a positive integer having a value of from 2 to 6; z has a value of 0 to 1; x has an average value of 5 to 3000; y has an average value of 0 to 3000 when z is 1, and y has an average value of 1 to 3000 when z is 0.

R" groups may be exemplified by, but not limited to, trimethylene, tetramethylene, pentamethylene, —$CH_2CH(CH_3)CH_2$—, and —$CH_2CH_2CH(CH_3)CH_2$— radicals. Preferable R" is a trimethylene or an alkyl substituted trimethylene radical such as —$CH_2CH(CH_3)CH_2$—.

R''' groups may be exemplified by, but not limited to methyl, ethyl, propyl, isoproplyl, butyl, and isobutyl.

A may be exemplified by, but not limited to, —$NH_2$, alkyl substituted amine radicals such as —$NHCH_3$, —$NHCH_2CH_2CH_2CH_3$, and aminoalkyl substituted amine radicals such as —$NHCH_2CH_2NH_2$, —$NH(CH_2)_6NH_2$ and —$NHCH_2CH_2CH_2N(CH_3)_2$.

In the above amine functional silicone formula when z is 0, the silicon has only pendent amine functional substituents; when z is 1, the amine functional substituents may be terminal or both terminal and pendant. In the above amine functional silicone, x is preferably from about 5 to 500 and y is preferably from 0 to 100 when z is 1 and from 1 to 100 when z is 0. Most preferably, x+y is in the range of about 15 to 1000.

The amine content (the number of amine functional groups in the molecule of the amine functional silicone) is generally expressed as mole percent amine. Mole percent amine is determined according to the relationship y/DP× 100, where y is the value of integer y in the above formula for the amine functional silicone and DP (Degree of Polymerization) is x+y+2 which indicates the chain length of the amine functional silicone.

Amine functional silicones useful herein are well known in the art and are commercially available.

Siloxane (I) may also be an epoxy functional silicone. Epoxy functional silicones of the general structure shown below can be used, in which subscript a represents an integer of one or more.

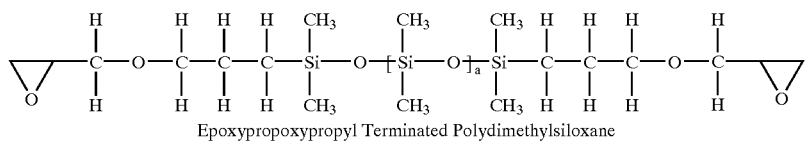
Epoxypropoxypropyl Terminated Polydimethylsiloxane

Epoxy functional silicones are well known in the art and available commercially. Such silicones have a viscosity ranging from 1 to about 200 centistoke (mm²/s) and molecular weights of about 300–6,000.

During the emulsification siloxane (I) is reacted with a crosslinker (II) wherein said crosslinker (II) contains Z and/or Z' groups with the proviso that when Y in siloxane (I) contains Z groups, the crosslinker contains Z' groups; when Y in siloxane (I) contains Z' groups, the crosslinker contains Z groups; and when Y in siloxane (I) contains Z and Z' groups, the crosslinker contains Z groups, Z' groups or both. In addition to Z and/or Z' groups the crosslinker can contain functional groups, F, as described above.

The crosslinker (II) can be organic compounds such as organic amines, organic epoxides or siloxanes of the general formula provided for siloxane (I), above. The amount of crosslinker (II) will depend on the amount of reactive sites in the either Z and/or Z' groups in siloxane (I) and the molecular weight of siloxane (I) (i.e. —NHCH$_2$CH(CH$_3$)CH$_2$NHCH$_2$CH$_2$NH$_2$ groups contains three reactive sites). One skilled in the art will be able to readily calculate the amount of crosslinker needed to ensure partial or complete reaction between the Z and Z' groups. Typically the ratio of reactive sites in the Z to Z' groups is from 0.1:1 to 1.5:1, preferably 0.2:1 to 0.5:1, more preferably 0.25:1 to 0.35:1.

Organic epoxides containing at least two epoxy groups suitable for use herein include ethylene glycol diglycidyl ether, diethylene glycol diglycidyl ether, polyethylene glycol diglycidyl ether, glycerine diglycidyl ether, triglycidyl ether, propylene glycol diglycidyl ether, and butanediol diglycidyl ether; 1,2,3,4-diepoxybutane; 1,2,4,5-diepoxypentane; 1,2,5,6-diepoxyhexane; 1,2,7,8-diepoxyoctane; 1,3-divinylbenzene diepoxide; 1,4-divinylbenzene diepoxide; 4,4'-isopropylidene diphenol diglycidyl ether, and hydroquinone diglycidyl ether. Other polyglycidyl ethers of alkane polyols, polyglycidyl ethers of poly(alkylene glycols), diepoxy alkanes, diepoxy aralkanes, and polyphenol polyglycidyl ethers, can also be used herein. Alternatively chlorohydrins may be used in place of or in conjunction with the epoxides.

Two especially preferred organic epoxides containing at least two epoxy groups are shown below, in which n is a positive integer determining the molecular weight of the epoxide.

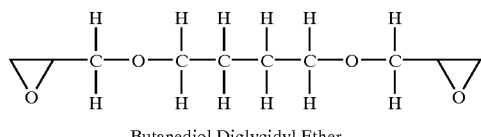
Butanediol Diglycidyl Ether

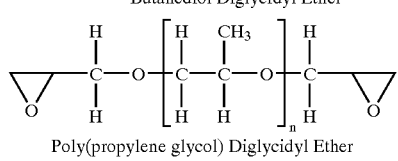
Poly(propylene glycol) Diglycidyl Ether

Organic amine compounds useful herein include ethane semicarbazole, acetaldehydeammonia, acetamide, dichloroacetamide, thioacetamide, acetamidine, o-aminoacetophenone, acrylamide, adalin, adipamide, allanturic acid, ethyl ester of allophanic acid, allylamine, ammelide, tert-amylamine, aniline, n-benzohydryl, 2,4-dibromo-6-nitroaniline, o-ffuoroaniline, p-nitrosoaniline, ar-pentachloroaniline, pp'-thiodianiline, anisamide, m-anisidine, 9,10-anthradiamine, anthranilaldehyde, methyl ester of anthranilic acid, 3-nitroanthranilic acid, anthranilonitrile, 2-amino-1-hydroxyanthraquinone, arsanilic acid, L-aspartic acid, p-aminoazobenzene, 5,5 diallyl-barbituric acid, 5 (2 furfurylidene)-2 thiobarbituric acid, benzalhydrazine, benzamidoxime, benzamidine, benzenepentamine, benzenesulfonamide, 3 ethoxybenzidine, benzidine sulfone, benzocaine, p-aminobenzohydrol, benzohydrazide, 3-amino-5-nitrobenzoic acid, o-sulfamylbenzoic acid, 2,2'-diaminobenzophenone, biguanide, acetylbiuret, bornylamine, 2-aminobutanol, cadaverine, 3-aminocamphor, dithiocarbamic acid, thiolcarbamic acid-ethyl ester, thionocarbamic acid-ethyl ester, thiocarbanilide, 1,5-diphenylearbohydrazide, m-aminocinnamic acid, 3-amino-o-cresol, crotonamide, cyanamide, cyclohexylamine, L-cysteine, diethylenetriamine, ethoxyamine, formamide, formohydrazide, Dfructosamine, guanidine, p-bromophenylhydrazine, piperazine, o-nitrophenylhydrazine, lactamide, nicotinamide, ethyloxamate, oxamide, pararosaniline, 2-phenanthrylamine, 2 nitrophenetidine, p-aminothiophenol, 2-aminopyridine, 4-aminoquinoline, thiosemicarbazide, sulfanilamine, tetradecylamine, 3-thiophenesulfonamide, thiophenine, trifluoro-m-toluidine, 2-bromo-5-nitro-ptoluidine, urea, allylurea, allylthiourea, ethylideneurea, nitrourea, p-phenethylurea, vinylamine, sulfaguanidine, dimethylgallium amide, and aminophenylmercuric acetate.

Preferably the organic amine is selected from ammonia, diethylene triamine, ethylene diamine, methane diamine, m-phenylene diamine, methylene dianiline, benzohydrazide, guanidine, benzidene sulfone, thioacetamide, piperazine, p-amino benzoic acid, thiosemicarbizide, allanturic acid, p,p'-thiodianiline, p-bromophenyl hydrazine, benzene pentamine, and N,N'-dimethyl ethylene diamine If desired, crosslinkers (II) that contain a single Z or Z' group can be included as an additional component, in order to control the cross link density and the overall molecular weight of the silicone particle.

Functional groups such as polyether groups, quaternary ammonium salt groups, monohydroxy alcohol groups, polyhydroxy alcohol groups, carbohydrate groups, acrylate groups, ester groups, amide groups, carbonate groups, carboxylate groups, sulfonate groups, sulfate groups, halogen groups, trialkoxysilyl groups, or mixtures thereof, can be present in the silicone particle. Such functional groups may be present in the silicone particle by using an emulsion component that contains the functional group, using a siloxane (I) and/or crosslinker (II) that contains the functional group, reacting the functional group into the silicone particle during or following emulsification, and/or blending a component containing a functional group into the emulsion.

The amount of siloxane (I) and crosslinker (II) will depend on the amount of silicone particles desired. Typically the amount of particles is from 0.1 to 80 wt. % based on the total weight of the emulsion, preferably 10 to 80 wt. %, more preferably 40 to 60 wt. %.

The reaction between siloxane (I) and crosslinker (II) to produce the silicone particles is carried out while emulsifying. There should be at least one emulsion liquid (III) present. When there is only one emulsion liquid present that liquid forms one phase of the emulsion while the particles form the second phase of the emulsion. When there are two emulsion liquids present the silicone particles are typically suspended in one of the liquids and form one phase of the emulsion while the other liquid forms the other phase. Typically water is used as the emulsion liquid with the water forming the external phase of the emulsion and the silicone particles forming the internal phase of the emulsion.

The emulsion liquids can be chosen from, but not limited to, water, silicone fluids, polar organic compounds, and non-polar organic compounds, preferably water. The emulsion liquid is added in an amount of from 1 to 99.8 wt. % based on the total weight of the emulsion, preferably 10 to 80 wt. %, more preferably 35 to 45 wt. %. A mixture of liquids can be used to form a single phase so long as the liquids are miscible and form an essentially homogeneous mixture.

Silicone fluids may be exemplified by, but not limited to, methyl siloxanes and alkyl and/or aryl siloxanes containing functional groups wherein the functional groups do not react with or substantially change the reaction between Z and Z'. Preferred are volatile methyl siloxanes (VMS). VMS compounds correspond to the average unit formula $(CH_3)_jSiO_{(4-j)/2}$ in which j has an average value of 2 to 3. The VMS compounds contain siloxane units joined by Si—O—Si bonds. Representative siloxane units are monofunctional "M" units: $(CH_3)_3SiO_{1/2}$ and difunctional "D" units: $(CH_3)_2SiO_{2/2}$. The presence of trifunctional "T" units: $CH_3SiO_{3/2}$ results in the formation of branched linear or cyclic volatile methyl siloxanes. The presence of tetrafunctional "Q" units $SiO_{4/2}$ results in the formation of branched linear or cyclic volatile methyl siloxanes.

Linear VMS have the formula $(CH3)_3SiO\{(CH_3)_2SiO\}_kSi(CH_3)_3$ where k is 0–5. Cyclic VMS have the formula $\{(CH_3)_2SiO\}m$ where m is 3–9. Preferably, these volatile methyl siloxane have a boiling point less than about 250° C. and viscosity of about 0.65 to about 5.0 $mm^2/s$.

Representative linear volatile methyl siloxanes include, but are not limited to, hexamethyldisiloxane, octamethyltrisiloxane, decamethyltetrasiloxane, dodecamethylpentasiloxane, tetradecamethylhexasiloxane, and hexadecamethylheptasiloxane. Representative cyclic volatile methyl siloxanes are hexamethylcyclotrisiloxane; octamethylcyclotetrasiloxane, decamethylcyclopentasiloxane; and dodecamethylcyclohexasiloxane.

Representative branched volatile methyl siloxanes are heptamethyl-3-{(trimethylsilyl)oxy}trisiloxane, hexamethyl-3,3,bis {(trimethylsilyl)oxy}trisiloxane, and pentamethyl {(trimethylsilyl)oxy}cyclotrisiloxane.

The silicone fluid useful herein also includes using silicone fluids represented by formulas $R_3SiO(R_2SiO)_nSiR_3$ and $(R_2SiO)_p$ wherein R is as defined above. The value of subscript n is 0–80, preferably 5–20. The value of subscript p is 3–9, preferably 4–6. These polysiloxanes have a viscosity generally in the range of about 1–100 $mm^2/s$. Silicone fluids can also be used where n has a value sufficient to provide siloxane polymers with a viscosity in the range of about 100–1,000 $mm^2/sec$. Typically, n can be about 80–375. Illustrative of such silicone fluids are polydimethylsiloxane, polydiethylsiloxane, polymethylethylsiloxane, polymethylphenylsiloxane, and polydiphenylsiloxane.

Functional silicone fluids can also be employed as an emulsion liquid. Useful functional silicone fluids are represented by the formula $R_3SiO(RFSiO)nSiR_3$ where F is a functional group as defined above and is essentially unreactive with siloxane (I) and crosslinker (II). Examples of functional silicone fluids include, but are not limited to, are acrylamide functional siloxane fluids, acrylate functional siloxane fluids, carbinol functional siloxane fluids, carboxy functional siloxane fluids, chloroalkyl functional siloxane fluids, glycol functional siloxane fluids, ketal functional siloxane fluids, mercapto functional siloxane fluids, methyl ester functional siloxane fluids, perfluoro functional siloxane fluids, polyisobutylene (PIB) functional siloxane fluids, silanol functional siloxanes, and vinyl functional siloxane fluids.

Silicone fluids are exemplified in U.S. Pat. No. 5,948,855 issued Sep. 7, 1999, incorporated herein for its teaching of silicone fluids.

Polar organic compounds useful herein include monohydroxy alcohols such as ethyl alcohol and isopropyl alcohol; diols and triols such as propylene glycol, 2-methyl-1,3-propane diol $HOCH_2CH(CH_3)CH_2OH$, 1,2-hexanediol $CH_3(CH_2)_3CH(OH)CH_2OH$, and glycerol; glycerol esters such as glyceryl triacetate (triacetin), glyceryl tripropionate (tripropionin), and glyceryl tributyrate (tributyrin); and polyglycols such as polyethylene glycols and polypropylene glycols, among which are PPG-14 butyl ether $C_4H_9[OCH(CH_3)CH_2]_{14}OH$.

Non-polar organic compounds may be exemplified by, but not limited to, aromatic hydrocarbons, aliphatic hydrocarbons, alcohols, aldehydes, ketones, amines, esters, ethers, glycols, glycol ethers, alkyl halides, or aromatic halides. Representative compounds are alcohols such as methanol, ethanol, 1-propanol, cyclohexanol, benzyl alcohol, 2-octanol, ethylene glycol, propylene glycol, and glycerol; aliphatic hydrocarbons such as pentane, cyclohexane, heptane, Varnish Maker's & Painter's (VM&P) solvent, and mineral spirits; alkyl halides such as chloroform, carbon tetrachloride, perchloroethylene, ethyl chloride, and chlorobenzene; aromatic hydrocarbons such as benzene, toluene, ethylbenzene, and xylene; esters such as ethyl acetate, isopropyl acetate, ethyl acetoacetate, amyl acetate, isobutyl isobutyrate, benzyl acetate, and isopropyl palmitate; ethers such as ethyl ether, n-butyl ether, tetrahydrofuran, and 1,4-dioxane; glycol ethers such as ethylene glycol monomethyl ether, ethylene glycol monomethyl ether acetate, diethylene glycol monobutyl ether, and propylene glycol monophenyl ether; ketones such as acetone, methyl ethyl ketone, cyclohexanone, diacetone alcohol, methyl amyl ketone, and diisobutyl ketone; petroleum hydrocarbons such as petroleum jelly, mineral oil, gasoline, naphtha, kerosene, gas oil, heavy oil, and crude oil; lubricating oils such as spindle oil and turbine oil; and fatty oils such as corn oil, soybean oil, olive oil, rape seed oil, cotton seed oil, sardine oil, herring oil, and whale oil.

Non-polar organic compounds are described in U.S. Pat. No. 5,948,855 issued Sep. 7, 1999, herein incorporated by reference for its teaching of non-polar organic compounds. In particular the non-polar organic compounds can be fragrances, natural oils derived from animal, vegetable or mineral sources. Most preferred are cosmetic oils such as almond oil, apricot kernel oil, avocado oil, cacao butter (theobroma oil), carrot seed oil, castor oil, citrus seed oil, coconut oil, corn oil, cottonseed oil, cucumber oil, egg oil, jojoba oil, lanolin oil, linseed oil, mineral oil, mink oil, olive oil, palm kernel oil, peach kernel oil, peanut oil, rapeseed oil, safflower oil, sesame oil, shark liver oil, soybean oil, sunflower seed oil, sweet almond oil, tallow (beef) oil, tallow (mutton) oil, turtle oil, vegetable oil, whale oil, and wheat germ oil.

Additionally present is at least one surfactant (V). The surfactant is typically present in the amount of 0.1 to 40 wt. % based on the total composition. Preferably the surfactant is present in the amount of 2 to 20 wt. % based on the total composition and more preferably in the amount of 8 to 12 wt. %. The surfactant can be a nonionic, cationic, anionic, or a mixture of such surfactants. Most preferred are organic nonionic surfactants, but the nonionic surfactant can be one containing silicon atoms. Most preferred are alcohol ethoxylates $R^2$—$(OCH_2CH_2)_cOH$, most particularly fatty alcohol ethoxylates. Fatty alcohol ethoxylates typically contain the characteristic group —$(OCH_2CH_2)_cOH$ which is attached to fatty hydrocarbon residue $R^2$ which contains about eight to about twenty carbon atoms, such as lauryl ($C_{12}$), cetyl ($C_{16}$) and stearyl ($C_{18}$). While the value of "c" may range from 1 to about 100, its value is typically in the range of 2 to 40.

Some examples of suitable nonionic surfactants are polyoxyethylene (4) lauryl ether, polyoxyethylene (5) lauryl ether, polyoxyethylene (23) lauryl ether, polyoxyethylene (2) cetyl ether, polyoxyethylene (10) cetyl ether, polyoxyethylene (20) cetyl ether, polyoxyethylene (2) stearyl ether, polyoxyethylene (10) stearyl ether, polyoxyethylene (20) stearyl ether, polyoxyethylene (21) stearyl ether, polyoxyethylene (100) stearyl ether, polyoxyethylene (2) oleyl ether, and polyoxyethylene (10) oleyl ether. These and other fatty alcohol ethoxylates are commercially available under such names as ALFONIC®, BRIJ, GENAPOL®, LUTENSOL, NEODOL®, RENEX, SOFTANOL, SURFONIC®, TERGITOL®, TRYCOL, and VOLPO.

One especially useful nonionic surfactant is polyoxyethylene (23) lauryl ether, a product sold under the name BRIJ 35L by ICI Surfactants, Wilmington, Del. It has an HLB of about 16.9

Cationic surfactants useful in the invention include compounds containing quaternary ammonium hydrophilic moieties in the molecule which are positively charged, such as quaternary ammonium salts represented by $R^3R^4R^5R^6N^+X^-$ where $R^3$ to $R^6$ are alkyl groups containing 1–30 carbon atoms, or alkyl groups derived from tallow, coconut oil, or soy; and X is halogen such as chlorine or bromine, or X can be a methosulfate group. Most preferred are dialkyldimethyl ammonium salts represented by $R^7R^8N+(CH_3)_2X^-$, where $R^7$ and $R^8$ are alkyl groups containing 12–30 carbon atoms, or alkyl groups derived from tallow, coconut oil, or soy; and X is halogen or a methosulfate group. Monoalkyltrimethyl ammonium salts can also be employed, and are represented by $R^9N^+(CH_3)_3X^-$ where $R^9$ is an alkyl group containing 12–30 carbon atoms, or an alkyl group derived from tallow, coconut oil, or soy; and X is halogen or a methosulfate group.

Representative quaternary ammonium salts are dodecyltrimethyl ammonium bromide (DTAB), didodecyldimethyl ammonium bromide, dihexadecyldimethyl ammonium chloride, dihexadecyldimethyl ammonium bromide, dioctadecyldimethyl ammonium chloride, dieicosyldimethyl ammonium chloride, didocosyldimethyl ammonium chloride, dicoconutdimethyl ammonium chloride, ditallowdimethyl ammonium chloride, and ditallowdimethyl ammonium bromide. These and other quaternary ammonium salts are commercially available under such names as ADOGEN, ARQUAD, SERVAMINE, TOMAH, and VARIQUAT.

Examples of anionic surfactants include sulfonic acids and their salt derivatives; alkali metal sulfosuccinates; sulfonated glyceryl esters of fatty acids such as sulfonated monoglycerides of coconut oil acids; salts of sulfonated monovalent alcohol esters such as sodium oleyl isothionate; amides of amino sulfonic acids such as the sodium salt of oleyl methyl tauride; sulfonated products of fatty acid nitriles such as palmitonitrile sulfonate; sulfonated aromatic hydrocarbons such as sodium alpha-naphthalene monosulfonate; condensation products of naphthalene sulfonic acids with formaldehyde; sodium octahydro anthracene sulfonate; alkali metal alkyl sulfates such as sodium lauryl (dodecyl) sulfate $CH_3(CH_2)_{11}OSO_3Na$; ether sulfates having alkyl groups of eight or more carbon atoms; and alkylaryl sulfonates having one or more alkyl groups of eight or more carbon atoms.

Commercial anionic surfactants useful in this invention include triethanolamine linear alkyl sulfonate sold under the name BIO-SOFT N-300 by the Stepan Company, Northfield, Ill.; sulfates sold under the name POLYSTEP by the Stepan Company; and sodium n-hexadecyl diphenyloxide disulfonate sold under the name DOWFAX 8390 by The Dow Chemical Company, Midland, Mich.

There is also present in the emulsion composition an active ingredient (VI). The active ingredient is typically present in the amount of 10 to 50 wt. % based on the total composition. Preferably the surfactant is present in the amount of 2 to 20 wt. % based on the total composition and more preferably in the amount of 8 to 12 wt. %. The active ingredient may be reactive with the siloxane (I) or crosslinker (II) resulting in the active ingredient being bonded into the silicone particle from which it can later be released. Or the active ingredient can be blended into the composition resulting in it being encapsulated by the silicone particle.

Active ingredients useful herein include, but are not limited to sunscreens (i.e., an UV absorber/UV light stabilizer), fragrances, vitamins, drugs including activated antiperspirant salts such as aluminum chlorohydrate and aluminum-zirconium trichlorohydrate, and α-hydroxy acids such as glycolic acid, lactic acid, tartaric acid, and citric acid, i.e., fruit acids and mixtures thereof. Preferabley the active ingredient is a suscreen or fragrance. Vitamins and drugs which can be used are described in U.S. Pat. No. 5,948,855, herein incorporated by reference for its teaching of these actives. These active ingredients may be further exemplified by vitamin C, vitamin $B_1$, vitamin $B_2$, vitamin $B_6$, vitamin $B_{12}$, niacin, folic acid, biotin, and pantothenic acid.

Fragrances may be exemplified by, but not limited to, perfume ketones and perfume aldehydes.

Preferably the perfume ketone is selected for its odor character from buccoxime; iso jasmone; methyl beta naphthyl ketone; musk indanone; tonalid/musk plus; Alpha-Damascone, Beta-Damascone, Delta-Damascone, Iso-Damascone, Damascenone, Damarose, Methyl-Dihydrojasmonate, Menthone, Carvone, Camphor, Fenchone, Alpha-Ionone, Beta-Ionone, Gamma-Methyl so-called Ionone, Fleuramone, Dihydrojasmone, Cis-Jasmone, Iso-E-Super, Methyl-Cedrenyl-ketone or Methyl-Cedrylone, Acetophenone, Methyl-Acetophenone, Para-Methoxy-Acetophenone, Methyl-Beta-Naphtyl-Ketone, Benzyl-Acetone, Benzophenone, Para-Hydroxy-Phenyl-Butanone, Celery Ketone or Livescone, 6-Isopropyldecahydro-2-naphtone, Dimethyl-Octenone, Freskomenthe, 4-(1-Ethoxyvinyl)-3,3,5,5,-tetramethyl-Cyclohexanone, Methyl-Heptenone, 2-(2-(4-Methyl-3-cyclohexen-1-yl)propyl)-cyclopentanone, 1-(p-Menthen-6 (2)-yl)-1-propanone, 4-(4-Hydroxy-3-methoxyphenyl)-2-butanone, 2-Acetyl-3,3-Dimethyl-Norbomane, 6,7-Dihydro-1,1,2,3,3-Pentamethyl-4(5H)-Indanone, 4-Damascol, Dulcinyl or Cassione, Gelsone, Hexalon, Iso-cyclemone E, Methyl Cyclocitrone, Methyl-Lavender-Ketone, Orivon, Para-tertiary-Butyl-Cyclohexanone, Verdone, Delphone, Muscone, Neobutenone, Plicatone, Veloutone, 2,4,4,7-Tetramethyl-oct-6-en-3-one, and Tetrameran.

More preferably, the perfume ketones are selected for its odor character from Alpha Damascone, Delta Damascone, Iso Damascone, Carvone, Gamma-Methyl-lonone, Iso-E-Super, 2,4,4,7-Tetramethyl-oct-6-en-3-one, Benzyl Acetone, Beta Damascone, Damascenone, methyl dihydrojasmonate, methyl cedrylone, and mixtures thereof.

Preferably, the perfume aldehyde is selected for its odor character from adoxal; anisic aldehyde; cymal; ethyl vanillin; florhydral; helional; heliotropin; hydroxycitronellal; koavone; lauric aldehyde; lyral; methyl nonyl acetaldehyde; P. T. bucinal; phenyl acetaldehyde; undecylenic aldehyde; vanillin; 2,6,10-trimethyl-9-undecenal, 3-dodecen-1-al, alpha-n-amyl cinnamic aldehyde, 4-methoxybenzaldehyde, benzaldehyde, 3-(4-tert butylphenyl)-propanal, 2-methyl-3-(para-methoxyphenyl propanal, 2-methyl-4-(2,6,6-trimethyl-2(1)-cyclohexen-1-yl) butanal, 3-phenyl-2-propenal, cis-/trans-3,7-dimethyl-2,6-octadien-1-al, 3,7-dimethyl-6-octen-1-al, [(3,7-dimethyl-6-octenyl)oxy] acetaldehyde, 4-isopropylbenzyaldehyde, 1,2,3,4,5,6,7,8-octahydro-8,8-dimethyl-2-naphthaldehyde, 2,4-dimethyl-3-cyclohexen-1-carboxaldehyde, 2-methyl-3-(isopropylphenyl)propanal, 1-decanal; decyl aldehyde, 2,6-dimethyl-5-heptenal, 4-(tricyclo[5.2.1.0(2,6)]-decylidene-8)-butanal, octahydro-4,7-methano-1H-indenecarboxaldehyde, 3-ethoxy-4-hydroxy benzaldehyde, para-ethyl-alpha, alpha-dimethyl hydrocinnamaldehyde, alpha-methyl-3,4-(methylenedioxy)-hydrocinnamaldehyde, 3,4-methylenedioxybenzaldehyde, alpha-n-hexyl cinnamic aldehyde, m-cymene-7-carboxaldehyde, alpha-methyl phenyl acetaldehyde, 7-hydroxy-3,7-dimethyl octanal, Undecenal, 2,4,6-trimethyl-3-cyclohexene-1-carboxaldehyde, 4-(3)(4-methyl-3-pentenyl)-3-cyclohexen-carboxaldehyde, 1-dodecanal, 2,4-dimethyl cyclohexene-3-carboxaldehyde, 4-(4-hydroxy-4-methyl pentyl)-3-cylohexene-1-carboxaldehyde, 7-methoxy-3,7-dimethyloctan-1-al, 2-methyl undecanal, 2-methyl decanal, 1-nonanal, 1-octanal, 2,6,10-trimethyl-5,9-undecadienal, 2-methyl-3-(4-tertbutyl)propanal, dihydrocinnamic aldehyde, 1-methyl-4-(4-methyl-3-pentenyl)-3-cyclohexene-1-carbox aldehyde, 5 or 6 methoxyOhexahydro-4,7-methanoindan-1 or 2-carboxaldehyde, 3,7-dimethyloctan-1-al, 1-undecanal, 10-undecen-1-al, 4-hydroxy-3-methoxy benzaldehyde, 1-methyl-3-(4-methylpentyl)-3-cyclhexenecarboxaldehyde, 7-hydroxy-3,7-dimethyl-octanal, trans-4-decenal, 2,6-nonadienal, paratolylacetaldehyde; 4-methylphenylacetaldehyde, 2-methyl-4-(2,6,6-trimethyl-1-cyclohexen-1-yl)-2-butena 1, ortho-methoxycinnamic aldehyde, 3,5,6-trimethyl-3-cyclohexene carboxaldehyde, 3,7-dimethyl-2-methylene-6-octenal, phenoxyacetaldehyde, 5,9-dimethyl-4,8-decadienal, peony aldehyde (6,10-dimethyl-3-oxa-5,9-undecadien-1-al), hexahydro-4,7-methanoindan-1-carboxaldehyde, 2-methyl octanal, alpha-methyl-4-(1-methyl ethyl) benzene acetaldehyde, 6,6-dimethyl-2-norpinene-2-propionaldehyde, para methyl phenoxy acetaldehyde, 2-methyl-3-phenyl-2-propen-1-al, 3,5,5-trimethyl hexanal, Hexahydro-8,8-dimethyl-2-naphthaldehyde, 3-propyl-bicyclo[2.2.1]-hept-5-ene-2-carbaldehyde, 9-decenal, 3-methyl-5-phenyl-1-pentanal, methylnonyl acetaldehyde, hexanal, trans-2-hexenal, 1-p-menthene-q-carboxaldehyde and mixtures thereof.

More preferred aldehydes are selected for its odor character from 1-decanal, benzaldehyde, florhydral, 2,4-dimethyl-3-cyclohexen-1-carboxaldehyde; cis/trans-3,7-dimethyl-2,6-octadien-1-al; heliotropin; 2,4,6-trimethyl-3-cyclohexene-1-carboxaldehyde; 2,6-nonadienal; alpha-n-amyl cinnamic aldehyde, alpha-n-hexyl cinnamic aldehyde, P.T. Bucinal, lyral, cymal, methyl nonyl acetaldehyde, hexanal, trans-2-hexenal, and mixture thereof.

In the above list of perfume ingredients, some are commercial names conventionally known to one skilled in the art, and also includes isomers. Such isomers are also suitable for use in the present invention.

Other active ingredients which can be carried in a phase (s) of the silicone fluid or non-polar organic compound include, but are not limited to vitamins and drugs among which are vitamin A, RETINOL, $C_2$–$C_{18}$ esters of RETINOL, vitamin E, tocopherol, esters of vitamin E, retinyl acetate, retinyl palmitate, retinyl propionate, α-tocopherol, tocophersolan, tocopheryl acetate, tocopheryl linoleate, tocopheryl nicotinate, tocopheryl succinate, and mixtures thereof. These active ingredients are described in U.S. Pat. No. 5,948,855, herein incorporated by reference for its teaching of these actives.

Optionally, there may be present a compound (VII) that introduces functional groups, F, into the silicone particle or emulsion ("functional compound") wherein F is as described above. The functional compound may be silicone, organic. It may be reactive with the siloxane (I) and/or crosslinker (II) resulting in functionality that is bonded directly to the silicone particle. It may be unreactive resulting in functionality that is in the emulsion. The functional compound can be added before, during or after the crosslinking reaction. Combinations of functional compounds can be used or combinations of functionality may be used so long as the functional compound does not substantially interfere with the crosslinking chemistry.

The silicone particles are prepared by combining the siloxane (I), crosslinker (II), at least one emulsion liquid (III), surfactant (IV), and active ingredient (V) while mixing sufficiently to produce the emulsion. Methods known in the art for producing emulsions can be used herein. The order of addition of components is not critical. Optional components and additional diluents may be added before, during or after the emulsification reaction has taken place.

Core-shell particles are typically formed by forming a first mixture comprising the active ingredient (V) with one reactant (siloxane or crosslinker), preferably an amine functional crosslinker; forming a second mixture comprising the other reactant, preferably an epoxy silicone with the emulsion liquid (III), preferably water and surfactant (IV) and thereafter combining and emulsifying the two mixtures. It is theorized that the reaction between siloxane (I) and crosslinker (II) takes place at the interface and forms a rigid particle, protecting the encapsulated material from the external phase.

Gel particles are typically formed by blending all of the components and thereafter emulsifying and reacting to form the particles.

Although heating is not required it is beneficial to heat while emulsifying. Typically the emulsion mixture is heated to a temperature of 25° C. to 150° C., preferably 50° C. to 100° C.

One of the benefits derived from silicone particles prepared according to this invention is their structural integrity against changes in such parameters as temperature, and the presence or absence of other components such as water, surfactants, and oils. Another benefit is their reduced permeability for entrapped active ingredients by the formation of crosslinked structures.

The silicone particles are useful in personal care products, for example, in preparing antiperspirants and deodorants. They can be used in skin creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers. They can be used in hair shampoos, hair conditioners, hair sprays, mousses, permanents, depilatories, and cuticle coats. In cosmetics they can be added to make-ups, color cosmetics, foundations, blushes, lipsticks, eyeliners, mascara, oil removers, color cosmetic removers, and powders. In such applications the compositions may include oil soluble, polar solvent soluble, and water-soluble ingredients such as vitamins as noted above.

These compositions are also capable of functioning as carriers for pharmaceuticals, biocides, herbicides, pesticides, and other biologically active substances; and they have utility as additives for cellulosic or synthetic nonwoven carrier substrates used in wet-like cleansing wipes such as wet-wipes, tissues, and towels, marketed generally for personal hygiene and household cleaning tasks.

EXAMPLES

The following non-limiting examples are provided so that one skilled in the art may more readily understand the invention.

Example 1

Water Phase
40.0 g DI water
10.0 g Tergitol TMN-6 (Ethoxylated trimethylnonanol)
2.0 g Lupasol WF (polyethyleneimine)
Oil Phase
40.0 g Damascone
8.0 g Octamethyl-3,5-Bis(Gamma-Glycidoxypropyl) Tetrasiloxane Each phase was mixed separately. The oil phase was added slowly to the water phase with mixing. The mixture was heated to 70° C. while mixing for 2 ½ hours. The resulting product was a creamy oil-in-water emulsion.

Example 2

Water Phase
39.0 g DI Water
5.0 g Lupasol WF (polyethyleneimine)
Oil Phase
40.0 g OMC (Octylmethoxycinnimate)
4.0 g Brij 30 (Polyoxyethylene (4) lauryl ether)
12.0 g Octamethyl-3,5-B is(Gamma-Glycidoxypropyl) Tetrasiloxane The oil and water phases were each mixed separatedly. The oil phase was slowly added to the water phase while mixing @ 700 rpm. The mixture was heated to 85° C.+/−2° C. with continuous mixing for 3 hours. The resulting product was a thick, creamy emulsion that was dilution stable. Under a microscope, rigid particles were evident.

Example 3

40.6 g Castor Oil
10.0 g Tergitol 15-S-3 Alcohol Ethoxylate
5.9 g Lupasol WF Polyethyleneimine
5.0 g Octamethyl-3,5-Bis(Gamma-Glycidoxypropyl) Tetrasiloxane All ingredients were mixed together and heated to 80° C. for 2 ½ hours. The resulting product was clear microemulsions gels.

Example 4

22 g Isopar M
8.0 g Delta-damascone
5.0 g Neodol 23-3 (Alcohol Ethoxylate)
3 g Lupasol WF (Polyethyleneimine)
12 g Octamethyl-3,5-Bis(Gamma-Glycidoxypropyl) Tetrasiloxane All ingredients were mixed together and heated to 80° C. for 2 ½ hours. The resulting product was clear microemulsions gels.

Example 5

| Oil Phase | |
| --- | --- |
| 2-8566 | 9.0% |
| Delta Damascone | 40% |
| Water Phase | |
| DI water | 40% |
| Tergital TMN-6 | 10% |
| Cross-linker | |
| 1,4-Butanediol Diglycidal Ether, 95% | 1% |

Components of oil phase were combined. Components of the water phase were combined and the oil phase was added to the water phase while mixing. The mixture was heated to about 80° C. with continued mixing for 1 hr. The cross-linker was added while continuing to mix and heat for 1 hour. The result was an oil-in-water emulsion having a very fine particle size.

What is claimed is:

1. A method for producing silicone particles where said method comprises emulsifying and reacting a composition comprising (I) a siloxane oligomer or polymer having units of

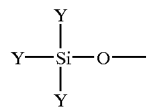

where each Y is independently selected from
O (oxygen radicals);
R': an alkyl group with 1 to 30 C atoms, an aryl group having 6 to 15 carbon atoms, an alkaryl group having 6 to 15 carbon atoms, and an aralkyl group having 6 to 15 carbon atoms;
Z: a reactive group selected from epoxy-functional groups or chlorohydrin functional groups;
Z': a functional group that reacts with epoxy-functional groups or chlorohydrin functional groups and;
F: functional group other than Z or Z',
with the proviso that at least 50 mol % of the Y groups in the siloxane are R', and there are at least two Z and/or Z' groups in the siloxane;

(II) a crosslinker wherein said crosslinker contains Z and/or Z' groups with the proviso that when Y in siloxane (I) contains Z groups, the crosslinker contains Z' groups; when Y in siloxane (I) contains Z' groups, the crosslinkor contains Z groups; and when Y in siloxane (I) contains Z and Z' groups, the crosslinker contains Z groups, Z' groups or both;

(III) at least one emulsion liquid;

(IV) a surfactant; and (V) an active ingredient selected from sunscreens, fragrances, vitamins, drugs, antiperspirant salts, and α-hydroxy acids.

2. The method as claimed in claim 1 wherein in siloxane (I) there are at least two Z' groups and the crosslinker (II) contains Z groups.

3. The method as claimed in claim 1 wherein in siloxane (I) there are at least two Z groups and the crosslinker contains (II) Z' groups.

4. The method as claimed in claim 1 wherein R' is a methyl group.

5. The method as claimed in claim 2 wherein the Z' group is an amino group and Z is an epoxy group.

6. The method as claimed in claim 3 wherein Z epoxy group and Z' is an amine group.

7. The method as claimed in claim 1 wherein siloxane (I) and crosslinker (II) are present in an amount to provide a ratio reactive sites in Z to Z' in a range of 0.1:1 to 1.5:1.

8. The method as claimed in claim 7 wherein the ratio in the range of 0.2:1 to 0.5:1.

9. The method as claimed in claim 7 wherein the ratio in the range of 0.25:1 to 0.35:1.

10. The method as claimed in claim 1 wherein siloxane (I) and crosslinker (II) are present in an amount so that the silicone particle comprises 0.1 to 80 wt. % of the composition.

11. The method as claimed in claim 1 where the emulsion liquid is water.

12. The method as claimed in claim 11 wherein water comprises 1 to 99.8 wt. % of the composition.

13. The method as claimed in claim 1 wherein the surfactant is present in an amount of 0.1 to 40 wt. % of the composition.

14. The method as claimed in claim 1 wherein the active ingredient is present in an amount of 10 to 50 wt. % of the composition.

15. The method as claimed in claim 1 wherein the active ingredient is a sunscreen.

16. The method as claimed in claim 1 wherein the active ingredient is a fragrance.

17. The method as claimed in claim 1 wherein the active ingredient reacts with the siloxane (I) and/or crosslinker (II).

18. The method as claimed in claim 1 wherein a first mixture comprising (II) and (V) is combined with a second mixture comprising (I), (III) and (IV) the combined mixture is thereafter emulsified and reacted.

19. The method as claimed in claim 1 wherein the reaction is carried out at a temperature in the range of 25° C. to 150° C.

20. A silicone particle produced by emulsifying and reacting a composition comprising (I) a siloxane oligomer or polymer having units of $$Y-\underset{\underset{Y}{|}}{\overset{\overset{Y}{|}}{Si}}-O-$$

where each Y is independently selected from

O (oxygen radicals)

R': an alkyl group with 1 to 30 C atoms, an aryl group having 6 to 15 carbon atoms, an alkaryl group having 6 to 15 carbon atoms, and an aralkyl group having 6 to 15 carbon atoms;

Z: a reactive group selected from epoxy-functional groups or chlorohydrin functional groups;

Z': a functional group that reacts with epoxy-functional groups or chlorohydrin functional groups (i.e. amine, hydroxyl); and F: a functional group other than Z or Z';

with the proviso that at least 50 mol % of the Y groups in the siloxane are R', and there are at least two Z and/or Z' groups in the siloxane;

(II) a crosslinker wherein said crosslinker contains Z and/or Z' groups with the proviso that when Y in siloxane (I) contains Z groups, the crosslinker contains Z' groups; when Y in siloxane (I) contains Z' groups, the crosslinker contains Z groups; and when Y in siloxane (I) contains Z and Z' groups, the crosslinker contains Z group, Z' groups or both;

(III) at least one emulsion liquid;

(IV) a surfactant; and (V) an active ingredient selected from sunscreens, fragrances, vitamins, drugs, antiperspirant salts, and α-hydroxy acids.

* * * * *